(12) United States Patent
Gonon

(10) Patent No.: US 6,508,823 B1
(45) Date of Patent: Jan. 21, 2003

(54) PNEUMATIC CONTROL HANDPIECE FOR SURGICAL AND MEDICAL USE

(75) Inventor: Bertrand Gonon, Lyons (FR)

(73) Assignee: Saphir Medical, Dardilly (FR)

( * ) Notice: Subject to any disclaimer, the term of this patent is extended or adjusted under 35 U.S.C. 154(b) by 0 days.

(21) Appl. No.: 09/334,914

(22) Filed: Jun. 17, 1999

(30) Foreign Application Priority Data

Jun. 17, 1998 (FR) .............................................. 98 07732

(51) Int. Cl.$^7$ .............................................. A61B 17/32
(52) U.S. Cl. .............................. 606/167; 606/1; 604/30; 604/35; 200/81 H
(58) Field of Search .............................. 604/27, 30, 35, 604/36, 44; 606/1, 159, 166, 167, 41, 42; 433/100; 200/81 H

(56) References Cited

U.S. PATENT DOCUMENTS

| | | | | |
|---|---|---|---|---|
| 3,494,363 A | * | 2/1970 | Jackson | ........................ 606/42 |
| 3,610,242 A | * | 10/1971 | Sheridan | ...................... 604/30 |
| 4,118,612 A | * | 10/1978 | Gabus | ........................ 200/81.4 |
| 4,299,221 A | * | 11/1981 | Phillips et al. | |
| 4,655,197 A | | 4/1987 | Atkinson | |
| 4,676,779 A | | 6/1987 | Mayoral | |
| 4,702,733 A | | 10/1987 | Wright et al. | |
| 4,857,047 A | * | 8/1989 | Amoils | ........................ 604/30 |
| 5,000,754 A | * | 3/1991 | DeOliveira et al. | ............ 606/42 |
| 5,195,959 A | * | 3/1993 | Smith | ........................ 606/42 |
| 5,322,506 A | | 6/1994 | Kullas | |
| 5,395,312 A | * | 3/1995 | Desai | ........................ 604/22 |
| 5,605,537 A | | 2/1997 | Ivey | |
| 5,674,226 A | | 10/1997 | Doherty et al. | ............. 606/107 |
| 5,735,815 A | | 4/1998 | Bair | ............................. 604/51 |
| 5,830,214 A | * | 11/1998 | Flom et al. | .................... 606/41 |

FOREIGN PATENT DOCUMENTS

| | | |
|---|---|---|
| DE | 30 19 115 A1 | 12/1981 |
| DE | 37 15 418 A | 11/1987 |
| EP | 0 346 712 A2 | 12/1989 |

(List continued on next page.)

*Primary Examiner*—Lee Cohen
(74) *Attorney, Agent, or Firm*—Armstrong, Westerman & Hattori, LLP

(57) ABSTRACT

The handpiece for use in a surgical or medical operation, includes means for generating instructions to control operation of at least one apparatus connected to the handpiece or associated with the surgical or medical operation through a pneumatic variation or a series of pneumatic variations in a fluid transported by at least one control conduit connecting the handpiece to a pressure or depression generator, the variation or series of variations being generated by a direct or indirect digital action by the operator on the control conduit or an opening of the conduit, the variation or series of variations being detected, then processed and exploited to remotely control the apparatus. The control method comprises generating at least one pressure or depression variation or discontinuity by a digital action on an area, a specific shape, or a key on the body of the handpiece connected by a conduit to a pressure or depression generator, the variation or discontinuity being detected by a detector or a sensor coupled to a circuit which generates a corresponding detection signal or detection signals, and the detection signal or detection signals being processed to control the operation of the apparatus, so that the handpiece constitutes a remote control for the apparatus concerned. The invention is of interest to handpiece manufacturers.

23 Claims, 7 Drawing Sheets

FOREIGN PATENT DOCUMENTS

| | | |
|---|---|---|
| EP | 0 470 781 A1 | 2/1992 |
| EP | 0 489 496 A1 | 6/1992 |
| EP | 0 551 920 A1 | 7/1993 |
| EP | 0 636 345 A1 | 2/1995 |
| EP | 0 879 578 A1 | 11/1998 |
| EP | 0 888 750 A1 | 1/1999 |
| WO | WO 94/10917 | 5/1994 |
| WO | WO 94 28807 | 12/1994 |
| WO | WO 96/01079 | 1/1996 |
| WO | WO 96/35469 | 11/1996 |
| WO | WO 96/39952 | 12/1996 |
| WO | WO 97/49441 | 12/1997 |
| WO | WO 98/55033 | 12/1998 |
| WO | WO 99/33510 | 7/1999 |

* cited by examiner

PNEUMATIC CONTROL HANDPIECE FOR SURGICAL AND MEDICAL USE

The present invention concerns a handpiece for surgical or medical use having an additional function as a remote control for at least one apparatus associated with the operation. The invention also concerns a corresponding control method.

This handpiece comprises a control or remote control function which operates by a modification of a flow rate, a pressure, or a depression, and more particularly a depression since in one embodiment, the handpiece is connected to a source of aspiration by at least one conduit coupled to at least one operation control sensor or detector.

BACKGROUND OF THE INVENTION

The handpiece according to the invention is in particular, but not exclusively, of the type of handpieces known for dissection operations, and also for washing-rinsing operations, in the surgical and medical fields. Thus, the handpiece is connected by at least one conduit to a source of high-pressure or flowing sterile liquid. A high-pressure or flowing jet tube, which is connected to a generator or distributor of sterile liquid, cuts through the handpiece. Control is performed by means of suitable sensors or detectors sensitive to pressure, depression, or flow rate.

Also known are handpieces in which the high-pressure jet tube is coupled to a suction tube. The instruction that makes it possible to alternate or add the cutting and/or aspiration functions is generally generated by modifying a parameter external to the handpiece. As a consequence, the operator must divert his or her attention to manipulate a knob or give an instruction which cannot be executed in real-time. As a result, the operation is slowed down or the formulated instruction lacks in precision, and in some cases, the manipulation is defective or awkward.

The handpiece according to the present invention is intended in particular for surgical use. The handpiece according to the invention makes it possible to perform precise and efficient cutting because the surgeon can control, alternatively or simultaneously with the tip of his or her fingers and without effort, the high-pressure jet function and the aspiration or cleaning/aspiration function, as well as the jet flow, without diverting his or her attention.

Such a handpiece can also be utilized advantageously in micro-mechanical applications or in any other field where high-quality cutting is desired.

The pressure control of the high-pressure jet or of the flow rate is generally performed by means of one or several electric switches located on the handpiece and connected by one or several wire connections.

In addition to the control by electric switch or switches, manual controls and various direct mechanisms are known in which elastically lifted plungers, in the manner of a musical wind instrument, act directly on the conduits and connections carrying the sterile liquid so as to limit or stop the flow rate.

In the case of a control by means of electric switch or switches, the wire connections and the processing of the low-current electrical control signals can be marred by transmission defects, interferences or various disturbances associated with the electrical and radio-electrical environment in the operation location. These perturbations lead to involuntary modifications to the handpiece operation and power and liquid supply. These defects correspond to risks which can lead to serious consequences.

In addition, the presence and the assembly of these wire connections in the apparatus constitute a nuisance and a loss of time.

In the case of direct manual control by mechanical plungers, there are other drawbacks. This technology requires manufacturing small, precisely-dimensioned special elements and mounting them on the handpiece. Thus, manufacturing and assembly costs constitute a first drawback. Other drawbacks correspond to the necessity of disinfecting and sterilizing the handpiece, which requires disassembling and reassembling all these elements, with various risks, including the possibility of losing various small components.

SUMMARY OF THE INVENTION

A goal of the present invention is to remedy these drawbacks by proposing a handpiece comprising controls located in the area of the operator's hand in the form of an opening or a manual pressure area of an open or closed conduit connected to a source of pressure or aspiration.

The pneumatic discontinuities or variations generated by temporarily sealing or freeing this opening or by a restriction resulting from a plastic or elastic deformation of the open or closed conduit by the operator are used for control at the level of the apparatus to which the handpiece is connected.

According to an essential characteristic, the handpiece according to the invention comprises, in addition to the high-pressure jet tube or the sterile liquid flow tube, one or several openings connected by one or several conduits to a source of pressure or depression, such as are available in operation locations, via sensors or detectors whose function is to inform the central unit of the apparatus that an instruction has been issued and is to be executed.

According to a preferred embodiment, these control openings are located on both sides of the high-pressure jet or liquid flow tube and open out symmetrically on the sides of the handpiece body.

According to another advantageous embodiment, these openings are located on ergonomic and anatomic conformations formed on the handpiece body in the area of the thumb and the forefinger of the operator so as to allow easy control with the fingers.

Control can be performed with the thumb alone and/or the forefinger of the operator which closes the opening of the control tube or tubes, or temporarily opens this opening which has remained closed, when the operator wants to send a control instruction. This control instruction is given quickly and easily without diverting the operator's attention. It generates a pressure or depression discontinuity, and therefore, an air flow discontinuity. The sensors or detectors provide the information to the central unit of the apparatus, which interprets the information and executes the corresponding instruction.

An alternative solution consists in locating in these ergonomic areas at least one section of a deformable conduit having an open or a closed extremity, which the operator can easily collapse by pressing one of his or her fingers, or in which the operator can easily generate a temporary leak, so as to generate a pressure or depression discontinuity, which is interpreted as an instruction. The deformable conduit may be constituted, for example, by the aspiration or evacuation conduit which would be stopped during a short period.

The direct control by the operator's hand allows higher precision and speed of the overall operation.

The pneumatic control is simple, clean, and insensitive to electrical and radio-electrical interferences, which are numerous in and around an operating room.

The present invention is also described in French Application No. 98/07732 filed on Jun. 17, 1999, which is hereby incorporated by reference.

BRIEF DESCRIPTION OF THE DRAWINGS

A preferred, non-limiting embodiment of the invention will now be described in reference to the annexed drawings in which.

DETAILED DESCRIPTION OF THE INVENTION

The present invention corresponds to the general inventive idea which consists in using a pneumatic discontinuity and more generally a pressure, depression, or flow rate variation generated by the operator's hand, during the operator's use of an aqua-dissection or washing-rinsing handpiece, to control the operation of the handpiece or of at least one apparatus connected to the handpiece or associated with the operation in which the handpiece is used.

More particularly, the invention consists in using at least one pneumatic connection connected to a source of pressure or depression and opening to the outside of the sugical or medical handpiece body by means of an opening, and in sealing this opening directly or indirectly with the operator's finger, or in causing a modification of the cross-section of a deformable section of a control conduit, to generate pneumatic signals which are used to control the operation of the handpiece after appropriate conversion by a sensor or a detector and transmission to the central unit of the apparatus for generating and distributing sterile operating liquid.

Figure 2:
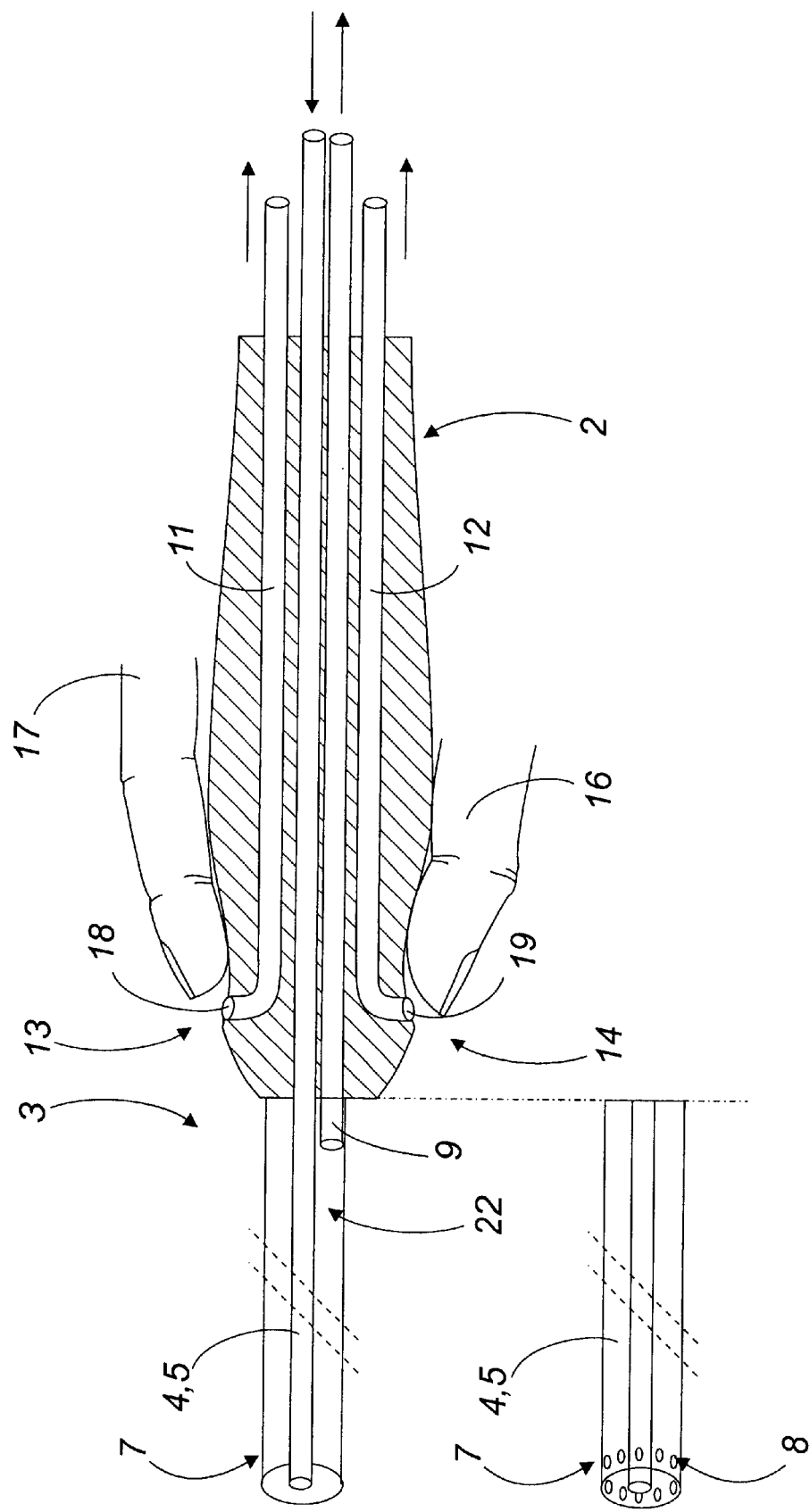
FIG. 2 is a general longitudinal cross-sectional view of a pneumatic control washing-rinsing handpiece according to the invention, comprising a washing jet tube and a parallel aspiration tube.
Figure 3:
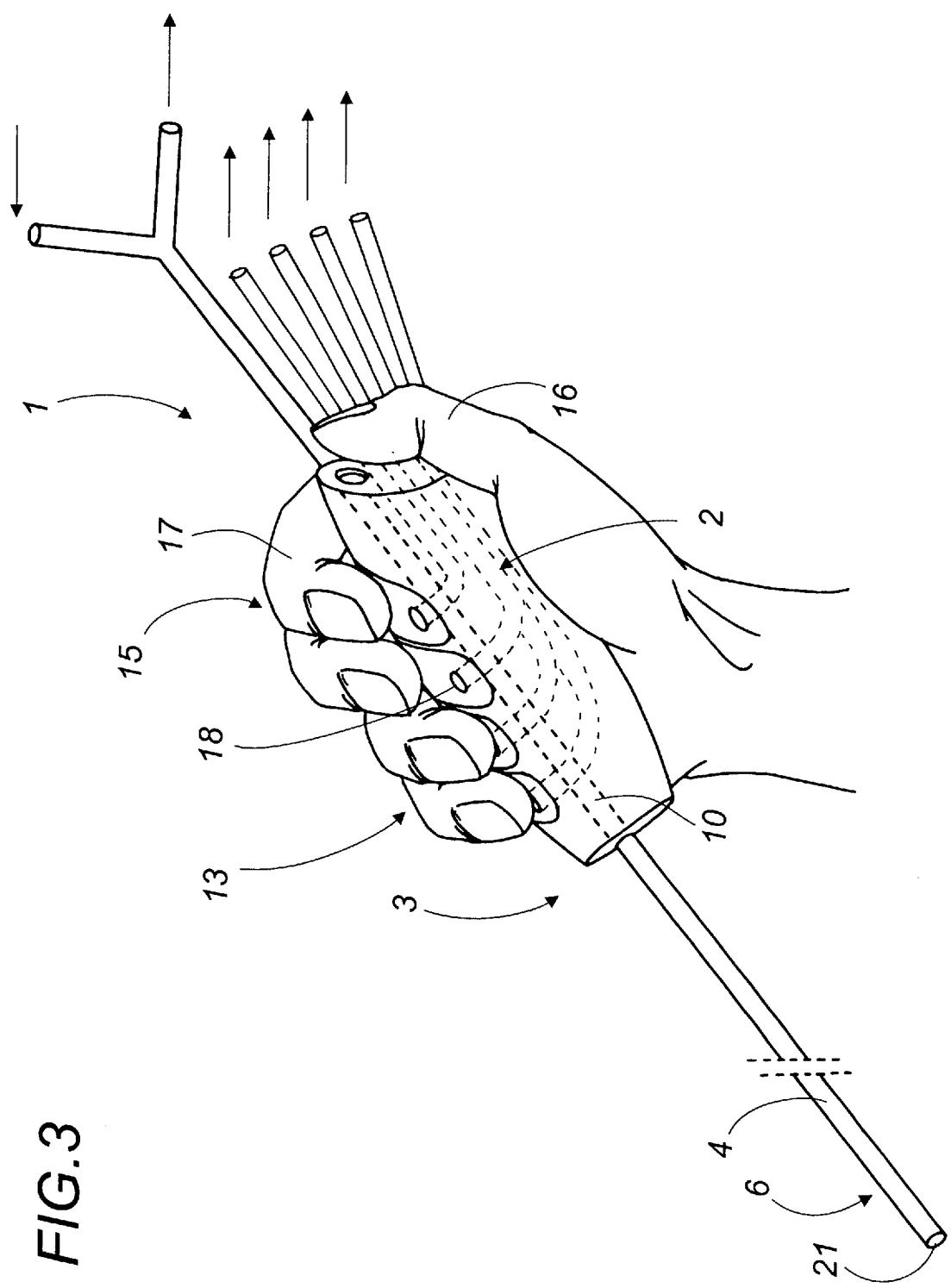
FIG. 3 is a general longitudinal cross-sectional view of a pneumatic control handpiece for ophtalmoscopy according to the invention, comprising several pneumatic control conduits and corresponding openings.

As shown in the figures, the handpiece 1 comprises a body 2 and a head 3. A high-pressure jet tube 4 or a washing jet tube 5 for delivering the sterile operating liquid to the operation area cuts through the handpiece 1 and opens out for example beyond the head 3 of the handpiece 1 on a projection 6 or inside an end sleeve 7 which is simple or has an annular perforated area 8 (FIG. 2). This tube 4 or 5 is connected to an apparatus for generating or distributing a high-pressure or flowing sterile liquid, which comprises a control circuit by means of which it can receive and execute control signals generated by a pneumatic control.

The high-pressure jet tube 4 and the washing jet tube 5 are often associated with an aspiration conduit 9 connected to a source of depression, for example to the vacuum system of the operation room. Of course, the aspiration conduit 9 of the washing-rinsing handpiece has a larger section than the aspiration conduit of the high-pressure handpiece. These conduits are intended to suction and evacuate the operating liquid along with residues, debris, scraps, splinters, fragments, etc., generated by dissecting, scraping, disintegrating with the high-pressure jet, or carried along when washing or rinsing.

Figure 1:
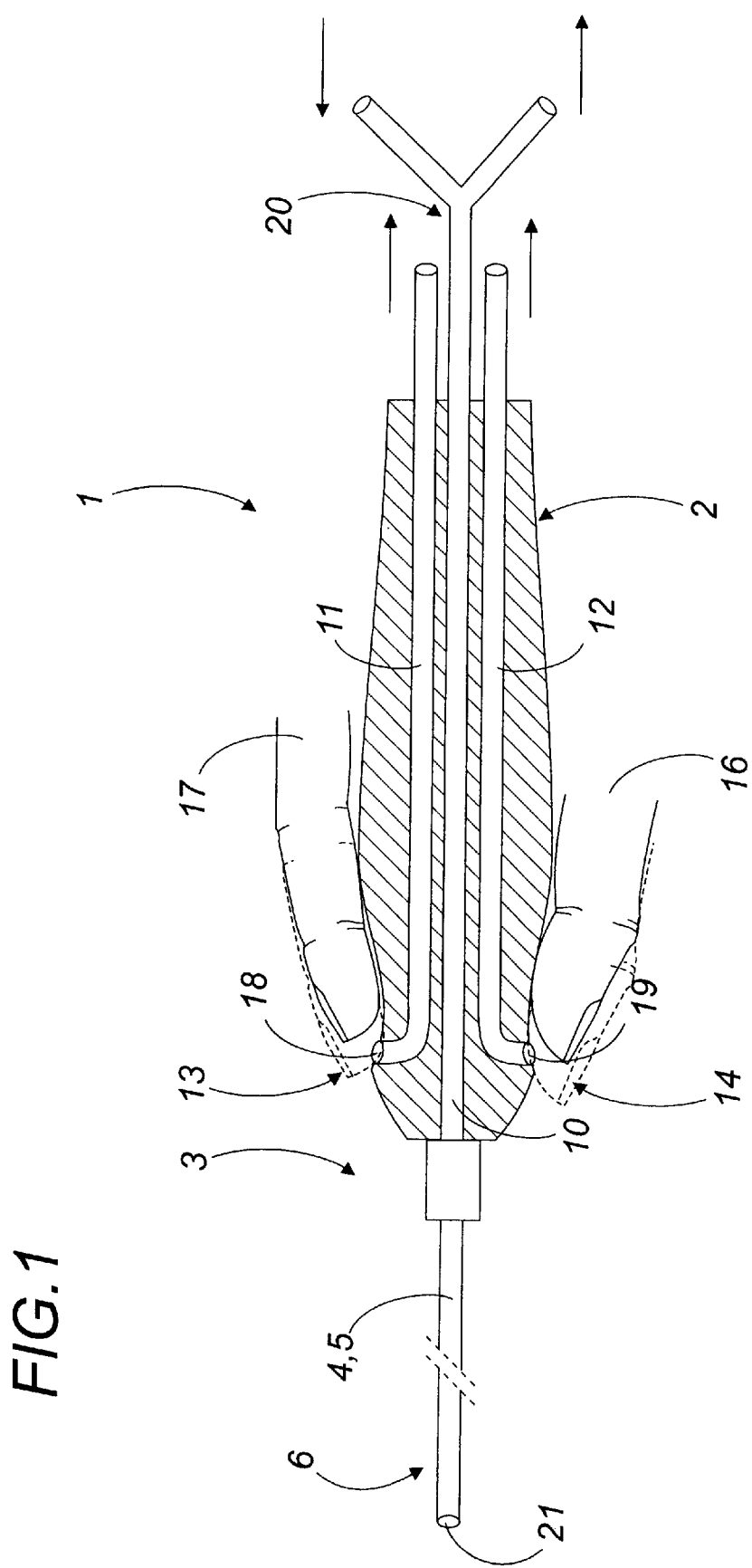
FIG. 1 is a general longitudinal cross-sectional view of a pneumatic control handpiece according to the invention, comprising a common high-pressure jet tube and two control conduits.
Figure 4:
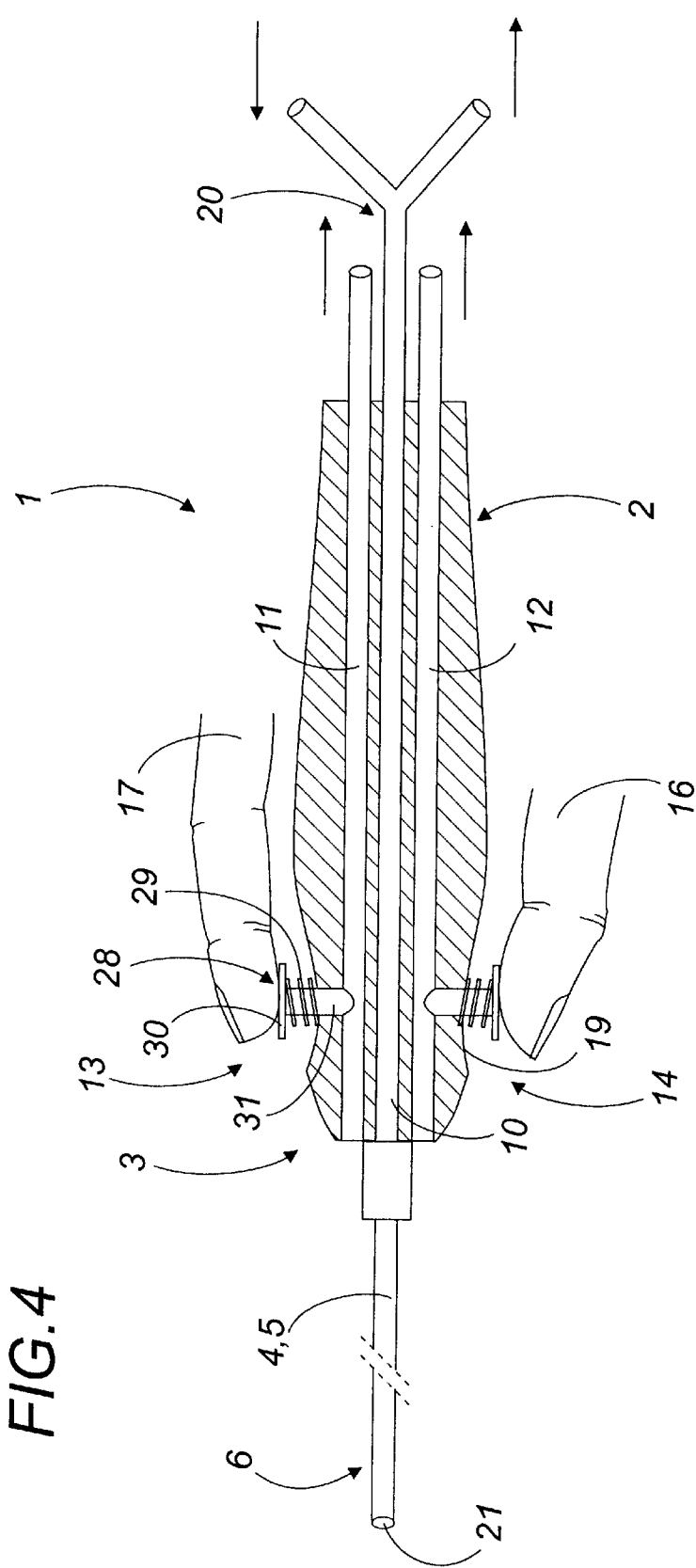
FIG. 4 is a general longitudinal cross-sectional view showing an alternative embodiment comprising push buttons.
Figure 6:
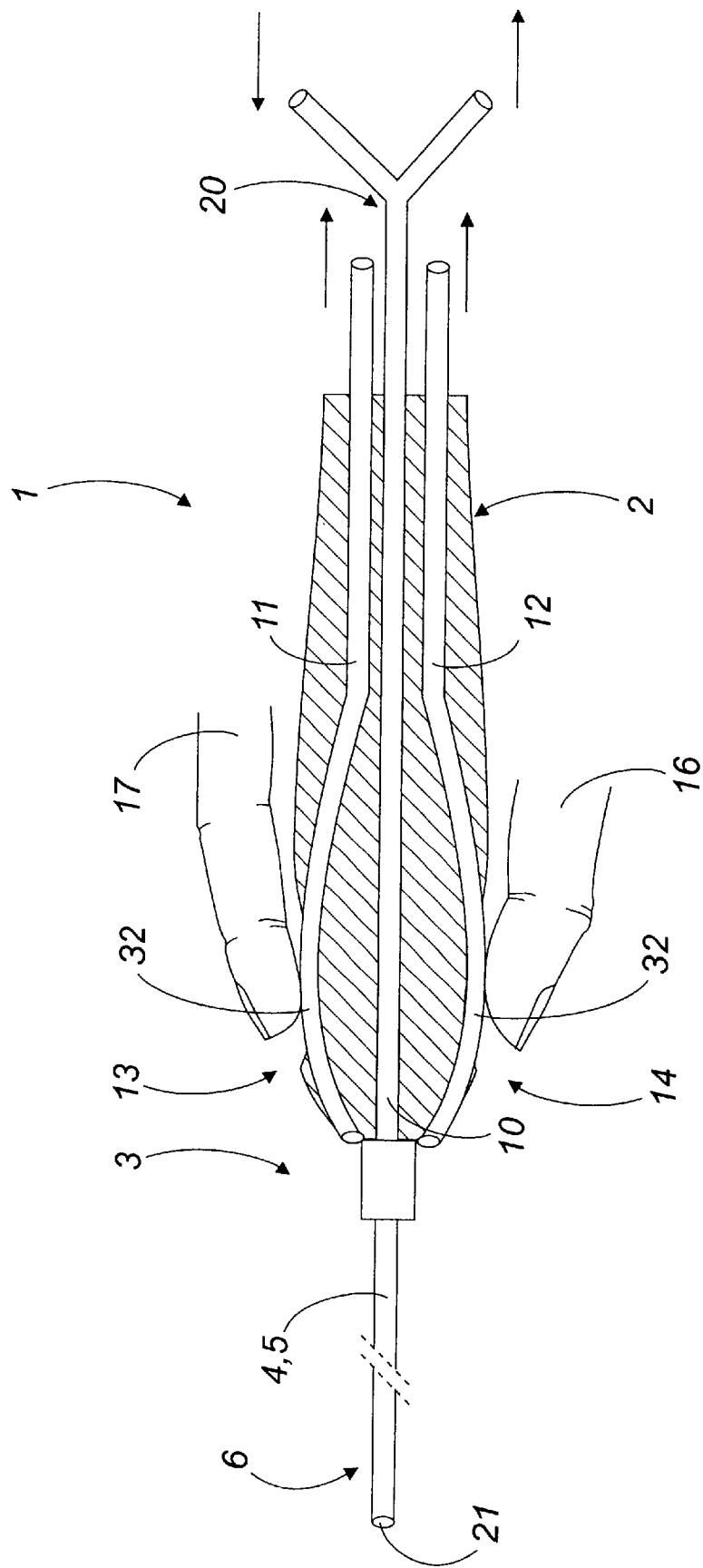
FIG. 6 is a general longitudinal cross-sectional view showing an alternative embodiment for collapsing the pneumatic control conduit.

There exists also handpieces having a common conduit 10 for a sterile operating liquid jet and for aspiration, as shown on FIGS. 1, 4 and 6. In these handpieces, the two modes of operation must be sequential.

The present invention proposes to add at least one, and preferably two, pneumatic control conduits 11 and 12, which are incorporated in the handpiece 1. These control conduits 11, 12 are preferably flexible. They enter from the rear of the handpiece on both sides of the high-pressure jet tube 4 or the washing tube 5 and open out or form a projection for example symmetrically on the lateral sides of the body 2 of the handpiece 1 in the area of two corresponding ergonomic and anatomic conformations 13 and 14, which are formed on both sides of the body 2 of the handpiece 1 and are located in the area of the holding area of the handpiece by the operator's hand 15, more particularly in the area of the operator's thumb 16 and forefinger 17 (FIG. 1.)

Pneumatic control conduits 11 and 12 are connected to a source of pressure or depression via appropriate sensors or detectors ( for example, of the type of those shown on FIGS. 7 and 8), for example, flow rate sensors or pressure or depression discontinuity detectors. These pneumatic control conduits 11 and 12 can be connected for example to the vacuum system in operation rooms of hospitals, or to any vacuum pump or compressor. The sensors or detectors are capable of transforming the fluid pressure, depression, or flow rate discontinuity, or more generally variation, in these control conduits into an electrical signal, and are adapted to be inserted in an electronic circuit to inform the central unit of the apparatus for distributing sterile operating liquid that an instruction must be executed.

One of the detection techniques consists in detecting a pressure, depression, or flow rate discontinuity or variation in the control conduit caused by voluntarily sealing the end opening, or by a voluntary modification of the section of the flexible control conduit, directly or indirectly, by the operator's finger. This pressure, depression, or flow rate discontinuity or variation is transmitted to the central unit of the apparatus for generating or distributing sterile operating liquid to inform the central unit of the instruction and to trigger the corresponding operating change.

When the operator holds the handpiece in his or her hand, he or she can free or seal, directly or indirectly, the openings of the control conduits 11 and 12 with his or her thumb 16 and/or his or her forefinger 17. When he or she wants to send an instruction, it is sufficient to free or seal the opening or openings 18, 19 of the pressure or depression conduit or conduits 11, 12 in order to generate a pressure or depression discontinuity which will be detected by the corresponding detector or detectors or sensor or sensors.

It is also possible to code the number of control pulses, which makes it possible to increase the general control possibilities.

A single control conduit makes it possible to control only one variable, for example by varying its intensity. However, it is possible to broaden the control instruction by coding the number of control pulses. The presence of two control conduits 11 and 12 connected to two specific sensors or detectors makes it possible to alternate and/or add two functions or more. As a result, operation precision and speed are improved. By a simple direct or indirect action of the thumb 16 and/or the forefinger 17, the operator can alternatively or simultaneously act upon the conduit or tube 4 or 5 for delivering the sterile operating liquid and control another variable, for example, regulate aspiration.

If the central unit or if the detector or detectors, or the sensor or sensors, are connected to other apparatuses used during the surgical operation, or more generally during any intervention in which the handpiece is used, the operator can control the operation or the modification of certain parameters of these apparatuses by a simple digital action.

To this aim, it is sufficient if the operator, by a simple digital action, triggers a sealing action in the area of the opening on the handpiece which communicates with the pressure or depression generator. For example, in a particular embodiment, the number of a succession of sealing actions corresponds to a particular control instruction. This coded succession can correspond to a signal which is recognized as a specific signal corresponding to a specific instruction.

As a result, the surgeon is able to access and control very easily and without diverting his or her attention numerous parameters which play a role during the surgical operation.

The control system in two steps, one step for the generation of a coded succession by the operator and one step for the treatment of the signal by the central unit and execution of the instruction, has an additional advantage.

Indeed, the operator does not act directly on the operation parameters when he or she generates one or several pressure or depression variations. A direct control system for controlling these variables would require a manipulation, or at least a fast and precise movement by the operator, to obtain a quantified, reproducible, and possibly modulated pneumatic variation triggering a proportional variation of the parameter value.

Such a manipulation can result in lack of precision or error, which can lead to serious consequences in a field as specific as surgery.

By contrast, the control device according to the invention is more reliable and more precise, and the operator is assured to obtain execution of the instruction he or she initiated.

The sensors or detectors are components which are sensitive to pressure, depression, or flow rate. They send to the apparatus for generating or distributing the sterile operating liquid the information which will be converted by the central unit in an instruction to stop or restart generating the liquid jet, or to increase or lower the pressure, depression, or flow rate.

In the embodiment shown on FIGS. 1, 4 and 6, high-pressure and aspiration jet conduits 4 and 5 are formed inside the body 2 of the handpiece 1 by a single common tube 10, which comprises at one of its extremities a connection 20 of the two branches, and which opens out in the area of the head 3 by a single extremity 21. In this embodiment of the handpiece, the dissection and aspiration functions are therefore alternative.

There exists also dual-purpose handpieces, which are used as operating handpieces using a high-pressure jet, but also as washing-rinsing handpiece. In these dual-purpose handpieces, the controls are more numerous. Accordingly, it is appropriate to provide several control lines.

According to another embodiment shown on FIG. 2, high-pressure jet conduit 4 and washing-aspiration conduit 5 are kept separated inside the body 2 of the handpiece 1 and open out in the area of the head 3 as a bitubular structure 22.

Because of the required flow rate for the washing sterile liquid, the aspiration conduit 9 has a larger diameter than the washing jet tube 5. This embodiment makes it possible to use the cutting function and the aspiration function simultaneously, which makes it possible for the operator to work with speed and precision without being hampered by debris generated by his or her work.

Figure 5:
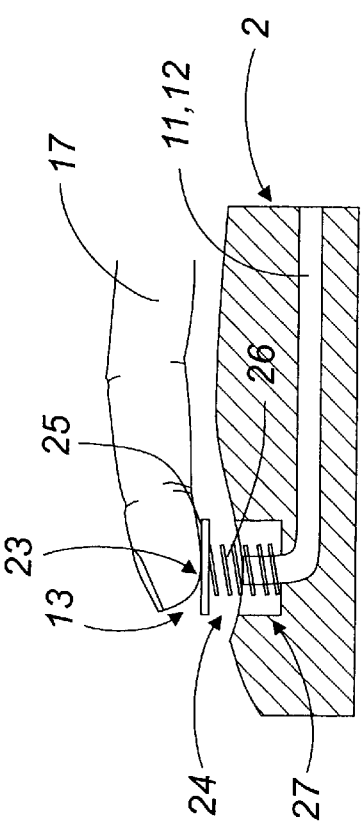
FIG. 5 is a partial longitudinal cross-sectional view showing an example of sealing element for sealing the control conduit.

In another embodiment shown on FIG. 5, the openings are sealed by an intermediary element 23, which is movable or deformable with elastic return freeing the opening, i.e., return toward a position away from the opening 18 or 19.

The intermediary element may be a sealing pad 24 mounted on at least two elastic washers or equivalent, or a special element comprising a sealing cap which is elastically lifted, for example by means of a spring 26, and a body in the form of a deformable sleeve 27 having a lateral face which is air-permeable. For example, a lateral surface in the form of a bellows having numerous openings, or with localized openwork, or a stacked structure formed by a succession of washers separated from each other by elastic means. Any similar or analog means, as well as any equivalent means, is suitable.

As indicated at the beginning of the description, any means which enables the operator to generate a pressure, depression, or flow rate discontinuity, or at least variation, by an action of one of his or her fingers on a handpiece for surgical or medical use, are included within the scope of the invention.

Thus, according to an embodiment of the invention shown on FIG. 4, push buttons such as 28 are each elastically lifted, for example by means of a spring 29. A top extremity of these push buttons is in the form of a key 30 and a bottom extremity is, for example, in the form of a non-cutting blade 31 in order to perform the necessary interruption of the flow.

Also, according to another embodiment of the invention shown on FIG. 6, the pressure or depression discontinuity or variation is caused by the elastic or plastic deformation of a deformable section 32 of the conduit connected to the source of pressure or depression. A sufficient length of this deformable section 32 projects partially or entirely in the area of the natural positioning area of the thumb 16, the forefinger 17, or another finger, in order to generate manually, directly or indirectly, a pressure or depression discontinuity or variation through a total or partial collapsing of the conduit in the area of this section. As mentioned above, this pressure or depression variation is converted and exploited as a control signal by the central unit of the apparatus for delivering the sterile operating liquid.

Of course, the collapsing of the conduit can be carried out by means of an intermediary element, for example an elastically lifted transverse element, so as to facilitate the collapsing and improve the throttling effect by restricting the passage until total sealing.

Other alternative embodiments, such as pinching, direct collapsing, or keys, are available.

According to another category of alternative embodiments, the detection does not correspond to an interruption of the flow, but occurs inversely. According to these alternative embodiments, the control conduit or conduits is or are permanently sealed or closed under a constant pressure or depression, and without flow. The control instruction is generated, in the case of a pressure control, by letting temporarily the gaseous fluid, for example air, escape, and in the case of a depression control, by admitting an amount of air by temporarily connecting the control conduit to ambient air.

Regarding technological means, the device may comprise inverted valves for the pressure as well as for the depression pneumatic control. These valves are located at the extremity of openings 18 or 19 of the control conduits 11 and 12. They are usually closed in the absence of an instruction, and they open temporarily upon manual action by the finger of the operator.

Processing of the control instruction in the area of the circuit does not present a difficulty. The instruction is also carried out based on the flow rate signal corresponding to the opening.

Also available are pinching or collapsing elements forced downward in a sealing position by a permanent pushing force which is temporarily eliminated, neutralized, compensated, etc., to initiate an instruction.

The alternative embodiments comprising a deformable section 32 are similarly constructed. The extremities of control conduits 11 and 12 are closed and an appropriate, manually controlled device generates a leak or a temporary communication with ambient air to initiate the instruction.

Figure 7:
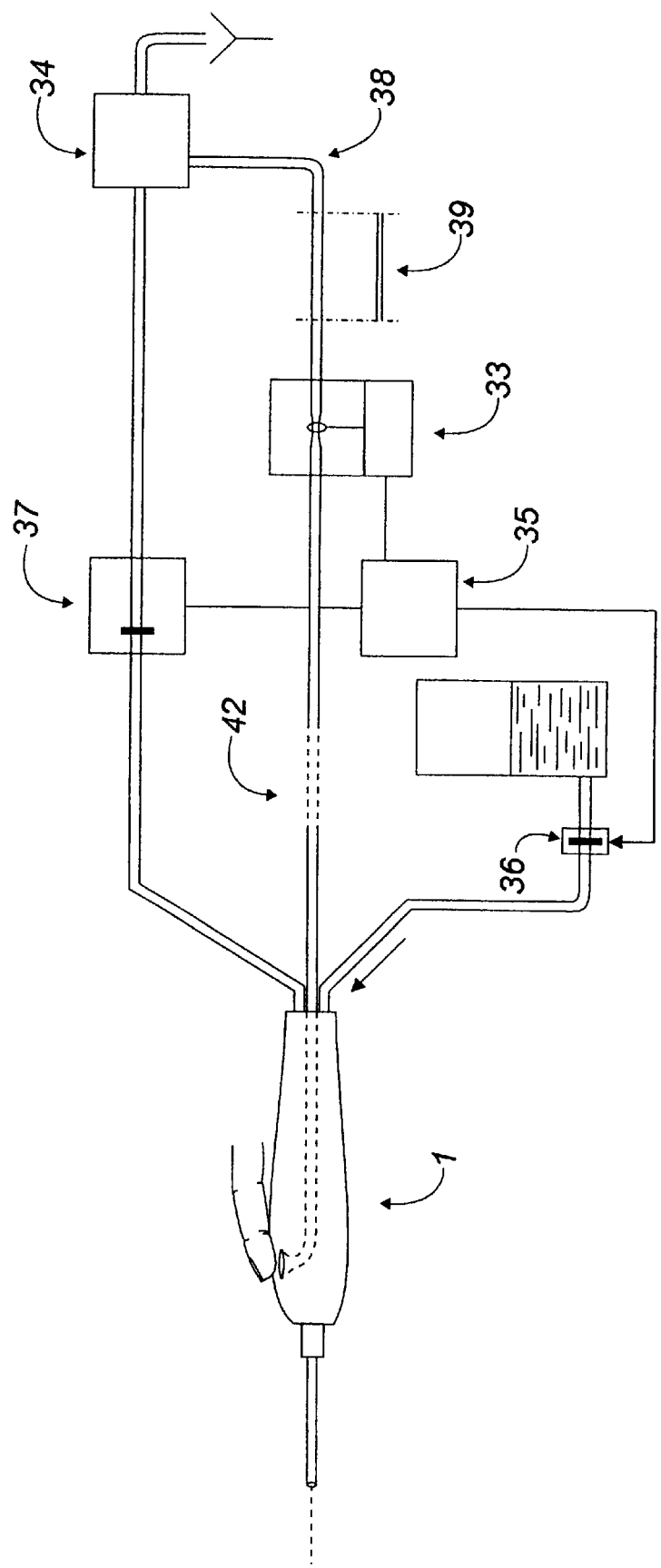
FIG. 7 is a schematic view of an example of assembly including the pneumatic control handpiece according to the invention.

The pneumatic pressure or depression discontinuity is preferably detected by measuring the flow rate or detecting the flow rate variation by means of a flow rate detector 33, which is utilized with a source of aspiration 24, for example in an assembly as shown on FIG. 7.

This detector is mounted in series in the aspiration and pneumatic variation control line or lines located between the handpiece and the depression generator.

The detector functions in a conventional way as a flow rate detector. The detection signal generated by the depression discontinuity is processed by an electronic circuit included in the detector 33 and coupled to the central unit 35 of the controlled apparatus or apparatuses. The central unit 35 can control for example only one apparatus, or the path or paths of an apparatus for generating a pulsed liquid jet delivered by the handpiece or any other apparatus for supplying power, fluid, pressure or depression to the handpiece, such as for example an apparatus for distributing operating liquid 36 and an apparatus for generating aspiration 37. In addition, the central unit 35 can control any other apparatus used in connection with the operation.

For security reasons, the detector signal is not taken into account until it reaches a certain level. This avoids false detections due to the involuntary passage of the operator's hand or sleeve, or any other perturbation, in the aspiration area of the control opening provided on the body of the handpiece.

To increase security even more, it is possible to try to increase the naturally existing, short time constant or delay between the manual control action and its detection, which is due to inertia in the detection chain.

To this aim, an interesting solution consists in limiting the flow rate by replacing, entirely or partially, the pneumatic conduit 38 connecting the detector 33 to the pressure or depression generator 34 by a section 39 having a smaller diameter. For simplicity, and to guaranty sterilization, this conduit 38 may be replaced in totality by a conduit having a smaller diameter, for example between the detector and the depression or pressure generator.

As the flow rate is even lower due to the smaller section of the conduit, the delay before detection occurs is increased. An involuntary action which is fugitive and brief in front of an aspiration and control opening on the handpiece will be without effect on the control.

Figure 8:
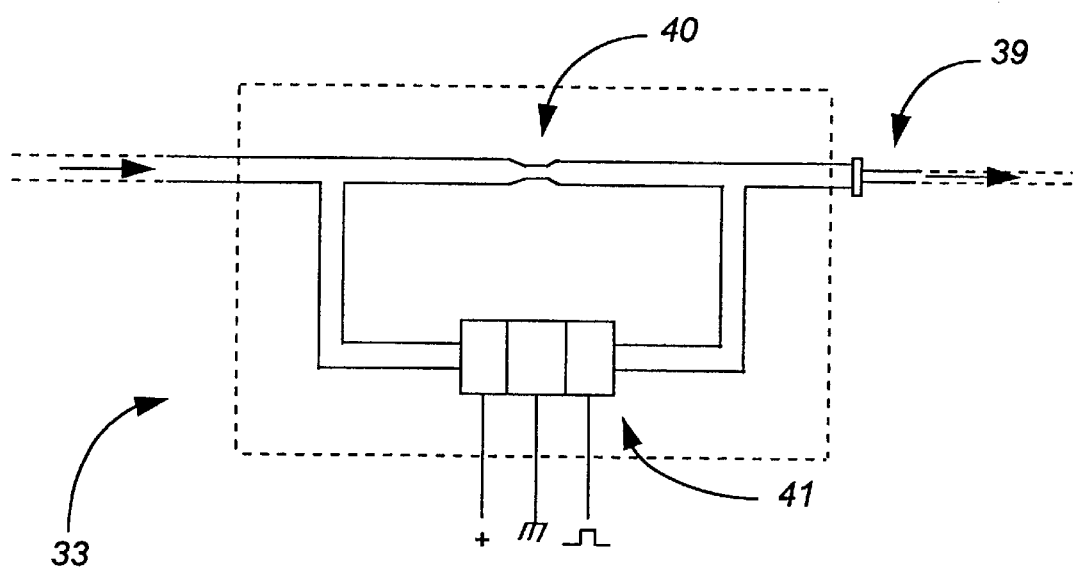
FIG. 8 is a cross-sectional view of an example of a pneumatic discontinuity detector.

FIG. 8 is intended to show the detector 33 as it is used in the example of assembly shown on FIG. 7, and as it can be used in practice.

This detector will now be described, it being understood that other detectors are also possible.

The detector shown on FIG. 8 comprises an air flow rate sensor manufactured and commercialized by the company HONEYWELL under the reference AVM300. The detector comprises a parallel branch 40 having a reduced and calibrated diameter, and the flow rate sensor made by HONEYWELL is mounted in parallel on the extremities of this parallel branch. The totality of the detector is incorporated in series in the conduit 42 connecting the control opening on the handpiece to the aspiration or pressure generator 34. The detector output increases from a tension of zero in the non-detecting state to a maximum tension of, for example, 5 volts during detection, then decreases to the initial state of zero. This signal comprising a voltage step is processed to control an apparatus associated with the use of the handpiece, for example the apparatus supplying the operating fluid and possibly the aspiration apparatus. A succession of digital actions by the operator is translated into an output in the form of a pulsatile stream or pulsed train which will be adequately processed to be used as an instruction.

The invention also concerns a process for controlling an apparatus associated with the operation in which the handpiece is used, according to which the operator generates one or several pressure or depression discontinuities or variations by digital action on an area, a specific conformation or a key on the body of the handpiece connected by a conduit to a pressure or depression conduit, and according to which this or other discontinuities are detected by a detector comprising a sensor coupled to a circuit for generating a detection signal or detection signals which are processed for controlling the operation of the apparatus or apparatuses associated with the operation in which the handpiece is used, so that the handpiece constitutes an actual remote control for the apparatus or apparatus concerned.

According to the above control process, the plurality of pressure or depression discontinuities or variations generated by a succession of digital actions by the operator on the handpiece is detected by the detector and transformed into detection signals and interpreted by a decoding circuit for remotely controlling the apparatus or apparatuses concerned.

What is claimed is:

1. Handpiece-controlled device for use in a surgical or medical operation, which comprises:
    a handpiece connected to at least one control conduit for connection to a pressure or depression generator, said handpiece comprising means for generating a pneumatic variation or a series of pneumatic variations in a fluid transported by said at least one control conduit, said pneumatic variation or series of pneumatic variations being generated by a direct or indirect digital action of an operator on said at least one control conduit or an opening of said at least one conduit,
    at least one apparatus connected to the handpiece or associated with the surgical or medical operation, said at least one apparatus connected to the handpiece or associated with the surgical or medical operation comprising a central operating unit, and a detector mounted in series on said at least one control conduit, said detector being coupled to said central operating unit of said at least one apparatus connected to the handpiece or associated with the surgical or medical operation, wherein said pneumatic variation or series of pneumatic variations are detected by said detector and transformed into an electrical signal which is transmitted to said central operating unit of said at least one apparatus connected to the handpiece or associated with the surgical or medical operation, such that the electrical signal is processed and exploited in the central operating unit to remotely control said at least one apparatus connected to the handpiece or associated with the surgical or medical operation.

2. Handpiece-controlled device according to claim 1, comprising liquid pressure generator for supplying a high-pressure and/or flowing sterile operating liquid, wherein said handpiece comprises a body and a head, a high-pressure jet conduit or flow conduit runs through the handpiece and opens out on the head of the handpiece, and said handpiece is connected to a said liquid pressure generator for supplying operating liquid to the handpiece.

3. Handpiece-controlled device according to claim 2, wherein an aspiration conduit runs through the handpiece, said aspiration conduit being connected to a source of aspiration or an aspiration generator.

4. Handpiece-controlled device according to claim 2, wherein said handpiece comprises two control conduits which run through the handpiece on respective sides of said jet conduit or flow conduit and comprise respective openings located symmetrically on lateral sides of the body of the handpiece in an area comprising ergonomic and anatomic conformations located in proximity to or in the area of the position of the thumb and the forefinger of a hand of the operator which holds the handpiece, said control conduits being connected to the pressure or depression generator via sensors or detectors sensitive to pressure, depression, or flow rate variation.

5. Handpiece-controlled device according to claim 1, wherein the pneumatic variation or series of pneumatic variations are depression or aspiration discontinuities.

6. Handpiece-controlled device according to claim 5, wherein said at least one control conduit is connected to a vacuum system of an operation room.

7. Handpiece-controlled device according to claim 1, wherein the pneumatic variation or series of pneumatic variations are pressure discontinuities.

8. Handpiece-controlled device according to claim 6, wherein said at least one control conduit is connected to a compressor.

9. Handpiece-controlled device according to claim 1, wherein the pneumatic variation or series of pneumatic variations are flow rate discontinuities.

10. Handpiece-controlled device according to claim 1, wherein said at least one control conduit is permanently closed and is temporarily opened to generate a control instruction.

11. Handpiece-controlled device according to claim 10, wherein said at least one control conduit comprises an opening which is closed by a valve, said valve being temporarily opened by a manual control action of the operator.

12. Handpiece-controlled device according to claim 1, wherein said at least one control conduit is permanently open and is temporarily closed to generate a control instruction.

13. Handpiece-controlled device according to claim 12, wherein said at least one control conduit comprises an opening on a lateral side of the handpiece in proximity to or in the area of a natural position of at least one finger of the operator, so that said operator can temporarily close the opening with said at least one finger, directly or through an intermediary closing element.

14. Handpiece-controlled device according to claim 13, wherein said handpiece comprises an intermediary closing element through which the operator can close the opening, and the intermediary element is an elastically lifted push button.

15. Handpiece-controlled device according to claim 14, wherein the intermediary element comprises a sealing head with elastic return to a position freeing the opening, which, in an operating position, is forced against the opening, said sealing head being connected to a deformable body through which air runs and which is retracted and airtight in the operating position of the sealing head.

16. Handpiece-controlled device according to claim 1, wherein said at least one control conduit comprises a section projecting or exposed in an area of manual control, which can be reached by a finger of the operator for a direct or indirect digital collapsing action.

17. Handpiece-controlled device according to claim 1, wherein the detector is a flow rate detector mounted in series in said at least one conduit connecting the handpiece to the depression or pressure generator.

18. Handpiece-controlled device according to claim 1, wherein said at least one control conduit or a section of said at least one control conduit between the detector and the depression or pressure generator has a reduced diameter.

19. Handpiece-controlled device according to claim 1, comprising at least another apparatus associated with the surgical or medical operation, wherein the pneumatic variation or series of pneumatic variations generated by the operator, after detection and processing, is or are used to control the operation of the at least one apparatus connected to the handpiece and the at least another apparatus associated with the surgical or medical operation.

20. Handpiece-controlled device according to claim 1, wherein the detector is a sensor which is modified by the pneumatic variation or series of pneumatic variations.

21. Handpiece-controlled device according to claim 1, wherein the central operating unit interprets a complex electrical signal corresponding to a plurality of said pneumatic variation or series of pneumatic variations successively detected by said detector as a single instruction for remotely controlling said at least one apparatus connected to the handpiece or associated with the surgical or medical operation.

22. Method for controlling with a handpiece an apparatus associated with an operation in which said handpiece is used by an operator, comprising:

generating at least one pressure or depression variation or discontinuity by a digital action of the operator on an area, a specific shape, or a key on the body of the handpiece, said handpiece being connected by a conduit to a pressure or depression generator, detecting said at least one pressure or depression variation or discontinuity by a detector or a sensor, generating an electrical detection signal or detection signals corresponding to said at least one pressure or depression variation or dicontinuity in a circuit to which said detector or sensor is coupled, and processing the detection signal or detection signals to control the operation of the apparatus, so that the handpiece constitutes a remote control for the apparatus concerned.

23. Method according to claim 22, comprising:

generating a plurality of pressure or depression variations or discontinuities by a succession of digital actions by the operator on the handpiece, and interpreting the detection signal or detection signals corresponding to said plurality of pressure or depression variations or discontinuities as a single instruction by a decoding circuit for remotely controlling the apparatus concerned.

* * * * *